(12) United States Patent
Sleeper et al.

(10) Patent No.: US 7,353,826 B2
(45) Date of Patent: Apr. 8, 2008

(54) SEALING NASAL CANNULA

(75) Inventors: Geoffrey P. Sleeper, Bay Village, OH (US); David J. Palkon, Tinley Park, IL (US)

(73) Assignee: Cardinal Health 205, Inc., Dublin, OH (US)

( * ) Notice: Subject to any disclaimer, the term of this patent is extended or adjusted under 35 U.S.C. 154(b) by 39 days.

(21) Appl. No.: 10/898,872

(22) Filed: Jul. 26, 2004

(65) Prior Publication Data

US 2005/0028822 A1 Feb. 10, 2005

Related U.S. Application Data

(60) Provisional application No. 60/493,515, filed on Aug. 8, 2003.

(51) Int. Cl.
*A61M 16/00* (2006.01)
*A61M 15/08* (2006.01)

(52) U.S. Cl. ............... 128/206.11; 128/207.18

(58) Field of Classification Search ........... 128/200.24, 128/202.18, 203.22, 200.26, 203.19, 203.29, 128/204.12, 205.25, 206.11, 206.12, 206.18, 128/206.21, 206.27, 206.28, 207.11, 207.13, 128/207.18, 202.27
See application file for complete search history.

(56) References Cited

U.S. PATENT DOCUMENTS

| 3,902,486 | A | 9/1975 | Guichard |
|---|---|---|---|
| 4,156,426 | A | 5/1979 | Gold |
| D262,322 | S | 12/1981 | Mizerak |
| 4,367,735 | A | 1/1983 | Dali |
| 4,774,946 | A | 10/1988 | Ackerman et al. |
| 4,782,832 | A | 11/1988 | Trimble et al. |
| 4,915,105 | A | 4/1990 | Lee |
| 4,919,128 | A | 4/1990 | Kopala et al. |
| 5,042,478 | A | 8/1991 | Kopala et al. |
| 5,269,296 | A | 12/1993 | Landis |
| 5,271,391 | A | 12/1993 | Graves |
| 5,443,075 | A | 8/1995 | Holscher |
| 5,477,852 | A | 12/1995 | Landis et al. |
| 5,533,506 | A | 7/1996 | Wood |
| 5,682,881 | A | 11/1997 | Winthrop et al. |
| 5,687,715 | A | 11/1997 | Landis et al. |

(Continued)

FOREIGN PATENT DOCUMENTS

WO    WO 00/74758    * 12/2000

(Continued)

OTHER PUBLICATIONS

60/448,465; 60/482,872; 60/488,810*

*Primary Examiner*—Teena Mitchell
(74) *Attorney, Agent, or Firm*—Baker Hostetler LLP

(57) ABSTRACT

An integrally molded ventilation interface includes a hollow bellows-like structure and two nasal prongs extending from a top surface of the bellows. A pair of headgear strap flanges can also be molded integrally with the ventilation interface. The nasal prongs provide a first sealing interface between an outer surface of the nasal prongs and an inner surface of the patient's nares. The bellows provides a second sealing interface between a top surface of the bellows-like structure and a bottom surface of a patient's nose. The headgear strap flanges provide a third sealing interface between the ventilation interface and a mustache region of the patient's face as well as a bottom surface of the patient's nose.

22 Claims, 9 Drawing Sheets

U.S. PATENT DOCUMENTS

| | | |
|---|---|---|
| 5,724,965 A | 3/1998 | Handke et al. |
| 5,752,510 A | 5/1998 | Goldstein |
| 6,119,694 A | 9/2000 | Correa et al. |
| 6,354,293 B1 * | 3/2002 | Madison .................. 128/204.13 |
| 6,405,729 B1 | 6/2002 | Thornton |
| 6,418,928 B1 | 7/2002 | Bordewick et al. |
| 6,431,172 B1 | 8/2002 | Bordewick |
| 6,478,026 B1 | 11/2002 | Wood |
| 6,581,601 B2 | 6/2003 | Ziaee |
| 6,595,215 B2 | 7/2003 | Wood |
| 6,644,315 B2 | 11/2003 | Ziaee |
| 6,679,265 B2 | 1/2004 | Strickland et al. |
| 6,691,707 B1 | 2/2004 | Gunaratnam et al. |
| 6,715,485 B1 * | 4/2004 | Djupesland ............ 128/203.15 |
| 6,776,162 B2 * | 8/2004 | Wood .................... 128/207.18 |
| 6,807,967 B2 * | 10/2004 | Wood .................... 128/207.18 |
| 2002/0059935 A1 | 5/2002 | Wood |
| 2003/0047185 A1 | 3/2003 | Olsen et al. |
| 2003/0116163 A1 | 6/2003 | Wood |
| 2003/0172936 A1 | 9/2003 | Wilkie et al. |
| 2003/0200970 A1 * | 10/2003 | Stenzler et al. ........ 128/207.18 |
| 2004/0065330 A1 | 4/2004 | Landis |
| 2004/0226566 A1 * | 11/2004 | Gunaratnam et al. .. 128/207.18 |
| 2005/0011524 A1 * | 1/2005 | Thomlinson et al. .. 128/207.18 |
| 2005/0199242 A1 * | 9/2005 | Matula et al. ......... 128/207.13 |
| 2005/0241644 A1 * | 11/2005 | Gunaratnam et al. .. 128/207.18 |
| 2006/0054169 A1 * | 3/2006 | Han et al. .............. 128/207.18 |
| 2006/0107958 A1 * | 5/2006 | Sleeper .................. 128/206.11 |
| 2006/0137690 A1 | 6/2006 | Gunaratnam et al. |

FOREIGN PATENT DOCUMENTS

| | | |
|---|---|---|
| WO | 2004/073778 | 9/2004 |
| WO | 2005/063328 | 7/2005 |

* cited by examiner

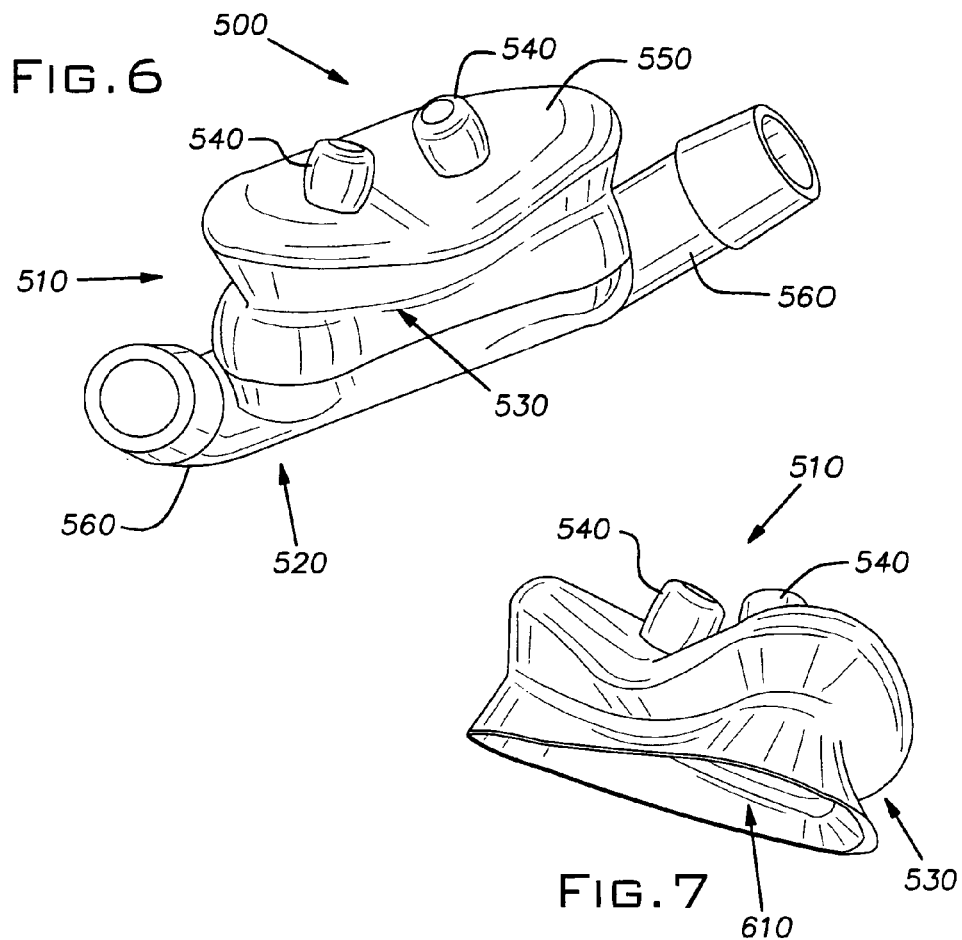
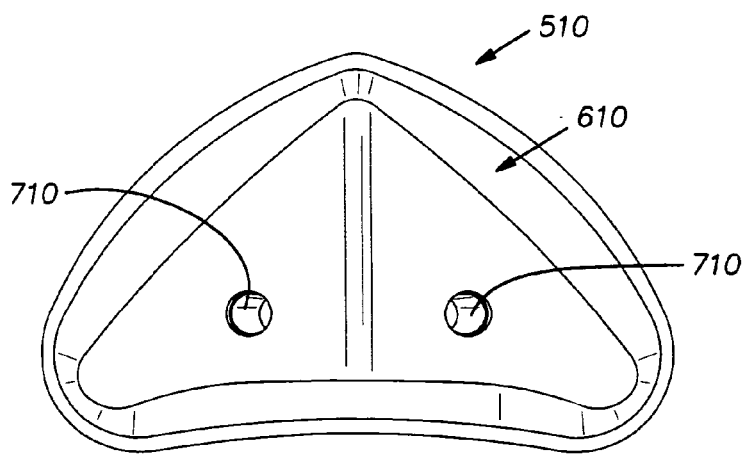

SEALING NASAL CANNULA

CROSS REFERENCE TO RELATED APPLICATIONS

The present invention claims priority to U.S. patent application Ser. No. 60/493,515, filed on Aug. 8, 2003.

FIELD OF THE INVENTION

The present invention relates generally to ventilation devices, and more particularly, to a nasal ventilation interface for a continuous positive airway pressure system.

BACKGROUND OF THE INVENTION

Sleep apnea is a potentially life-threatening breathing disorder characterized by brief interruptions of breathing during sleep. There are two types of sleep apnea: central and obstructive. Central sleep apnea, which is less common, occurs when the brain fails to send the appropriate signals to the breathing muscles to initiate respirations. Obstructive sleep apnea occurs when air cannot flow into or out of the person's nose or mouth although efforts to breathe continue. In a given night, the number of involuntary breathing pauses or "apneic events" may be as high as 20 to 60 or more per hour. Sleep apnea can also be characterized by choking sensations. The frequent interruptions of deep, restorative sleep often leads to excessive daytime sleepiness and may be associated with an early morning headache. Early recognition and treatment of sleep apnea is important because it may be associated with irregular heartbeat, high blood pressure, heart attack, and stroke.

Various forms of positive airway pressure during sleep can be an effective form of therapy for the apnea sufferer. Ventilation can be applied in the form of continuous positive airway pressure, in which positive pressure is maintained in the airway throughout the respiratory cycle; bi-level positive airway pressure system, in which positive pressure is maintained during inspiration but reduced during expiration; and intermittent (non-continuous) positive pressure, in which pressure is applied when an episode of apnea is sensed. In such procedures, a patient wears a mask over the nose during sleep, and pressure from an air blower forces air through the nasal passages. Typically, a thin flexible tube made of an inert material transports the air. The tube terminates in an opening that can be inserted into the patient's nostrils. A pair of smaller nasal insert tubes can protrude from the tube or the tube can split at a Y-junction into two smaller tubes, each smaller nasal insert tube carrying gas to one nostril, thereby increasing the fraction of inspired oxygen.

Conventional nasal tube systems do not provide a positive seal between the nasal insert tubes and the nostrils. Most nasal ventilation systems therefore include a mask that fits over the nose and is intended to provide a space of oxygen-enriched air for inhalation into the lungs for respiration. Such systems frequently suffer from air leaking out around the mask, creating an inability to assure ventilation in many patients. Additionally, most systems are usually very position dependent, whereby if the mask is moved slightly with respect to the facial contour or with respect to the nose, air leakage occurs. With such systems, the mask can become uncomfortable when not in position, thus requiring the patient to remain rather still in order to alleviate the discomfort and to maintain oxygen inspiration.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention relates to a ventilation interface for a continuous positive airway pressure system. According to a first aspect of the present invention, a ventilation interface is provided which includes a nasal cannula body. The nasal cannula body includes a pair of nasal prongs located on a top portion of the nasal cannula body to create a first sealing interface between the nasal cannula body and a nose; and a bellows-like structure integrally molded in a portion of the nasal cannula body to create a second sealing interface between the nasal cannula body and the nose.

According to another aspect of the present invention, a ventilation interface is provided having a nasal cannula body; and a pair of barrel shaped prongs located on a top portion of the nasal cannula body, the barrel shaped prongs providing a large sealing surface between an outer surface of the prongs and an inner surface of a patient's nares.

According to yet another aspect of the present invention, a ventilation interface is provided, the ventilation interface including a nasal cannula body; and a pair of nasal prongs located on a top portion of the nasal cannula body, the nasal prongs comprising a thin wall that inflates under pressure to create a sealing surface with nares of a patient.

According to yet another aspect of the present invention, the ventilation interface includes means for creating a first sealing interface between the ventilation interface and a patient's nose; means for creating a second sealing interface between the ventilation interface and the patient's nose; and means for creating a third sealing interface between the ventilation interface and the patient's nose.

According to yet another aspect of the present invention, a method of manufacturing a ventilation interface is provided. The method includes forming a nasal cannula body from a flexible material; forming a pair of nasal prongs materially integrally with the nasal cannula body; and forming a headgear strap materially integrally with the nasal cannula body.

The following description and the annexed drawings set forth in detail certain illustrative aspects of the invention. These aspects are indicative, however, of but a few of the various ways in which the principles of the invention may be employed and the present invention is intended to include all such aspects and their equivalents. Other objects, advantages and novel features of the invention will become apparent from the following detailed description of the invention when considered in conjunction with the drawings.

BRIEF DESCRIPTION OF THE DRAWINGS

FIG. 6 illustrates a perspective view of another nasal cannula body in accordance with an aspect of the present invention.

FIG. 7 illustrates a perspective view of a top portion of the nasal cannula body of FIG. 6 in accordance with an aspect of the present invention.

FIG. 8 illustrates a bottom view of the top portion of the nasal cannula body of FIG. 6 in accordance with an aspect of the present invention.

DETAILED DESCRIPTION OF THE INVENTION

Figure 1:
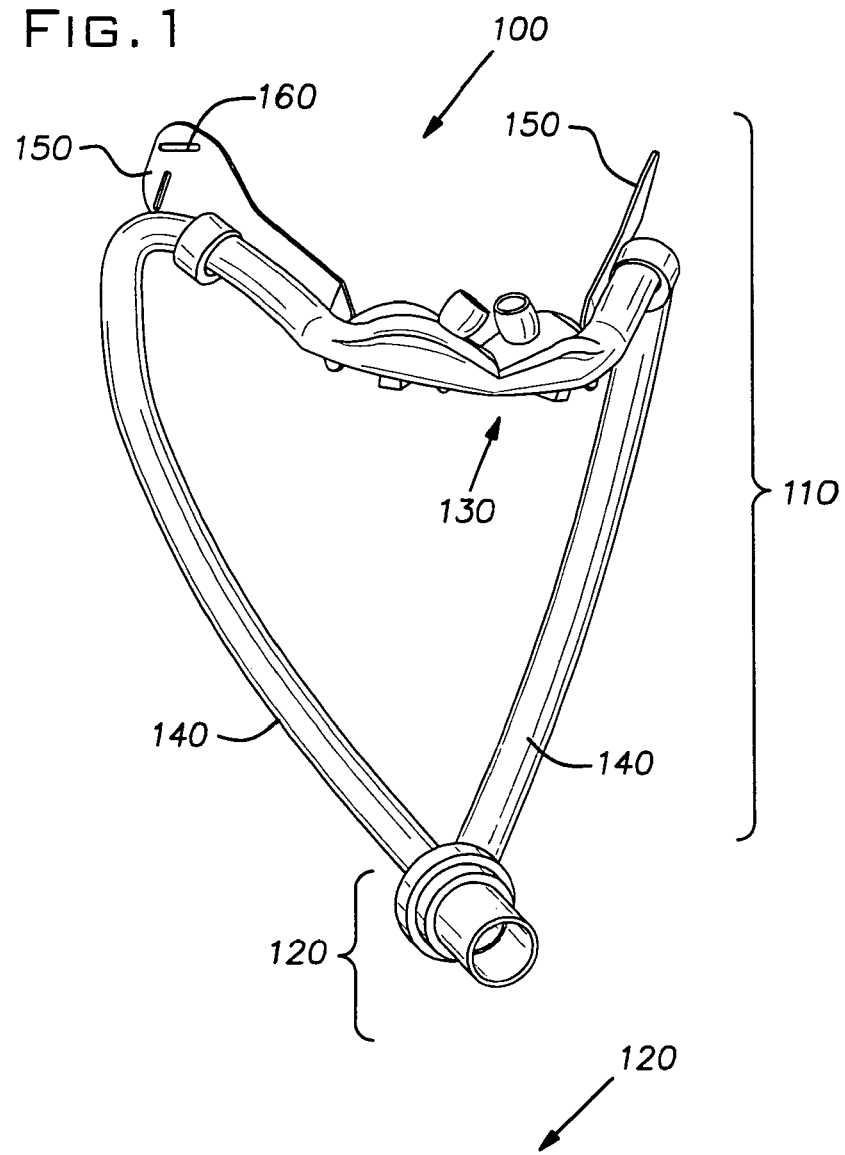
FIG. 1 illustrates a perspective view of a nasal ventilation interface in accordance with an aspect of the present invention.

The present invention provides a nasal ventilation interface having at least two sealing interfaces. The present invention will now be described with reference to the drawings, wherein like reference numerals are used to refer to like elements throughout. It is to be appreciated that the various drawings are not necessarily drawn to scale from one figure to another nor inside a given figure, and in particular that the size of the components are arbitrarily drawn for facilitating the reading of the drawings. In the following description, for purposes of explanation, numerous specific details are set forth in order to provide a thorough understanding of the present invention. It may be evident, however, that the present invention may be practiced without these specific details.

Turning initially to FIG. 1, an example of a nasal ventilation interface 100 in accordance with a first aspect of the present invention is illustrated. The nasal interface 100 comprises a base portion 110 and a swivel component 120. The base portion 110 includes a nasal cannula body 130 materially integral with two supply tubes 140. The base portion 110 is manufactured from one or more inert materials, such as polyurethane, silicone, or the like. The supply tubes 140 are employed to deliver air pressure from a ventilation device (not shown) to a patient via the nasal cannula body 130. In particular, the ventilation device forces a gas, such as air, through the supply tubes 140 and can be provided by a continuous positive airway pressure machine, a bi-level positive airway pressure machine, an intermittent (non-continuous) positive pressure machine, or any other suitable machine to deliver air to the patient.

For sleep apnea therapy, the ventilation device will usually supply room air at a pressure of between five and fifteen centimeters of water. The room air may be supplemented with oxygen if desired by splicing an oxygen supply line into the supply hose or using a triple port connector. It is normally unnecessary to humidify or add moisture to the air supplied by the ventilation device in using the nasal interface of the present invention, as the nasal interface is designed to avoid stripping moisture from the nares. Thus, moisture does not have to be added to relieve patient discomfort from drying or burning sensations in the nasal airways.

Figure 2:
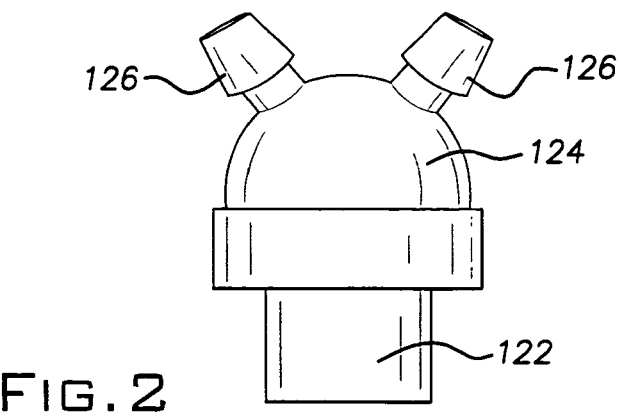
FIG. 2 illustrates a front view of a swivel component in accordance with an aspect of the present invention.

Each of the supply tubes 140 includes an end portion, which is coupled to the swivel component 120 to facilitate easy manipulation of the supply tubes 140 for patient comfort. Turning now to FIG. 2, the swivel component 120 comprises a substantially cylindrical element 122 for coupling with a tube of the ventilation device and a hemispherical element 124 having two tubular engaging portions 126 projecting therefrom. The two tubular engaging portions 126 are utilized for coupling with end portions of the supply tubes 140 of the ventilation interface 100. The cylindrical element 122 and the hemispherical element 124 are operable to swivel with respect to each other. For instance, the cylindrical element 122 and the hemispherical element 124 can swivel about each other by 360°. It is to be appreciated that any suitable structure contemplated for swiveling the ventilation interface 100 with the tube of the ventilation device can be utilized.

Turning back to FIG. 1, the nasal interface 100 also includes headgear strap flanges 150, which are coupled to the base portion 110, to facilitate utilization of headgear straps (not shown). Each of the headgear strap flanges 150 includes at least one aperture 160 for receiving a portion of the headgear straps therethrough. When nasal prongs of the nasal cannula body 130 are inserted into nares of the patient, the headgear strap fastens around the patient's head and applies backward pressure to the nasal cannula body 130. A first sealing interface is thus created via the headgear strap securing the nasal interface 100 against the patient's mustache region. In addition to this backward pressure, the flanges 150 are positioned in such a way that the headgear strap applies an angular, upward pressure (e.g., approximately a 45-degree angle) to a bellows portion of the nasal cannula body 130, which will be described in further detail below. This angular, upward pressure creates a second sealing interface between the nasal cannula body 130 and the patient's nose.

The supply tubes 140 can be shaped to extend along a base of the nasal cannula body 130 and bend downward near the headgear strap flanges 150. As a result, the headgear straps support weight and torque produced by the supply tubes 140, thereby decreasing the chance of the supply tubes 140 disturbing a sealing means and potentially breaking a seal between the ventilation interface 100 and the patient. Alternatively or additionally, the supply tubes 140 can be looped over the patient's ears.

Figure 3:
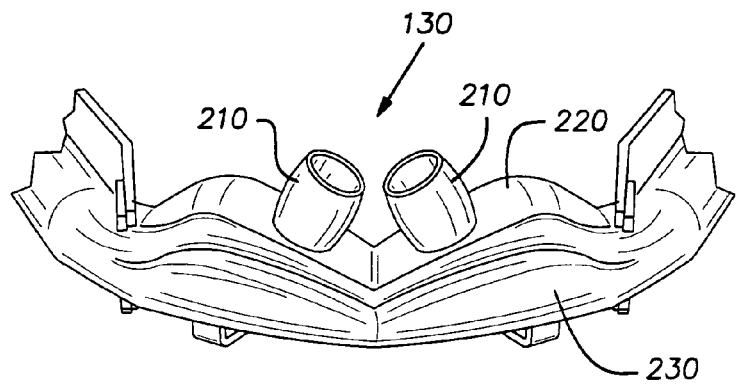
FIG. 3 illustrates a perspective view of the nasal cannula body employed in the nasal ventilation interface of FIG. 1 in accordance with an aspect of the present invention.

Turning now to FIG. 3, the nasal cannula body 130 of the ventilation interface 100 is shown in greater detail. The nasal cannula body 130 is an arcuate, hollow body formed of a flexible material, such as a silicone elastomer, for example. The nasal cannula body 130 includes two substantially barrel-shaped nasal prongs 210 projecting from a top surface 220 of the nasal cannula body 130 and formed materially integrally therewith. The nasal prongs 210 are hollow to form a continuous flow path, or conduit, for passage of inhaled and exhaled gases between the patient's nasal air passages and air chamber. Further, the nasal prongs 210 operably create a third sealing interface between the nasal prongs 210 and the patient's nares via the barrel-shaped structure. The 'barrel shape' is defined by a diameter of a central portion of the nasal prongs 210 being greater than diameters at end portions of the nasal prongs 210. Employing such a barrel shape structure creates a large, even sealing surface when inserted into the patient's nares. For instance, when inserted into the nares of the patient, the barrel shape of each of the prongs 210 is compressed in a radial direction such that a substantially uniform pressure is applied across the outer surface of each of the prongs 210 and against an inner surface of a respective naris, thus forming a substantially airtight seal between the prong 210 and the naris over a large surface area. The nasal prongs 210 also include a center-to-center distance that corresponds to a center-to-center distance between nares of an average user, such as about one centimeter. It is to be appreciated that any suitable center-to-center distance can be employed. Spacing the nasal prongs 210 by such a distance facilitates adjustment of the nasal interface 100 for patient comfort.

A bellows-like structure (hereinafter referred to as "bellows") 230 is integrally molded in the nasal cannula body 130 to create the second sealing interface between the nasal cannula body 130 and the patient's nose. More specifically, the second sealing interface is created between the top surface 220 of the nasal cannula body 130 and a bottom, triangular shaped area of the nose. The bellows 230 act in a manner similar to a compression spring to apply a gentle upward pressure to the nose thereby holding the sealing surfaces (e.g., the top surface of the bellows 230 and the bottom area of the nose) in sealing engagement with one another. The bellows 230 is adjustable in length between a contracted state and an expanded state.

Figure 4:
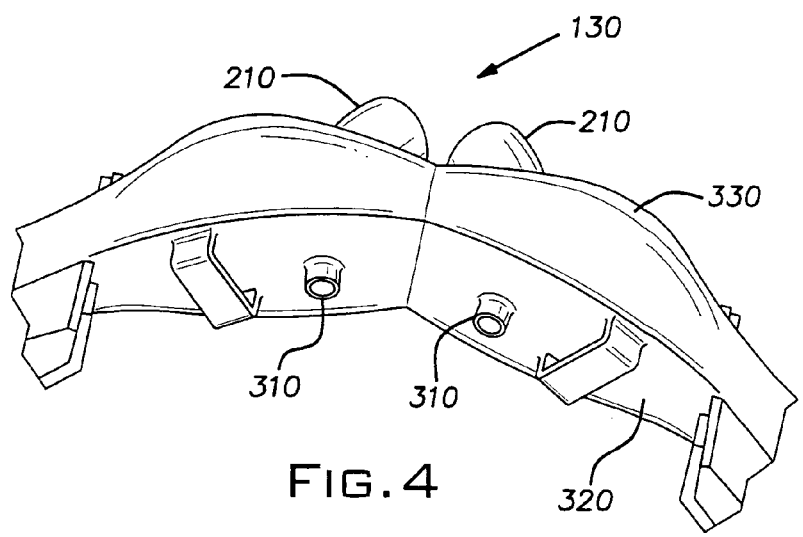
FIG. 4 illustrates another perspective view of the nasal cannula body employed in the nasal ventilation interface of FIG. 1 in accordance with an aspect of the present invention.

FIG. 4 depicts a bottom perspective view of the nasal cannula body 130. The nasal cannula body 130 further includes at least one bleeder port 310 projecting from a bottom surface 320 of the cannula body 130. In the example illustrated in FIG. 4, two bleeder ports 310 are utilized and are axially aligned with the nasal prongs 210. The bleeder ports can be cylindrical and have an internal diameter of about three millimeters and a length of about 0.25 inches, for example. The internal diameter of the bleeder ports 310 are ample to permit venting of carbon dioxide exhaled by the patient while not being so large as to cause a significant pressure drop in the cannula body 130. The axial alignment of the bleeder port 310 with the nasal prongs 210 creates a direct path for venting of the expired gases. At substantially the same time, laminar flow of air supplied by the supply tubes is normal to the bleeder ports 310, such that air supplied by the ventilator must bend about ninety degrees to exit through the bleeder ports 310. The effect of this construction is that the bleeder ports 310 are virtually silent in operation, mitigating a whistle noise associated with bleeder holes in conventional ventilation interfaces.

As illustrated in FIG. 4, the nasal cannula body 130 can also includes a substantially straight-shaped back surface 330. However, it is to be appreciated that the back surface 330 of the nasal cannula body 130 can also include the bellows-like structure formed in the front surface 230 of the nasal cannula body 130.

Figure 5:
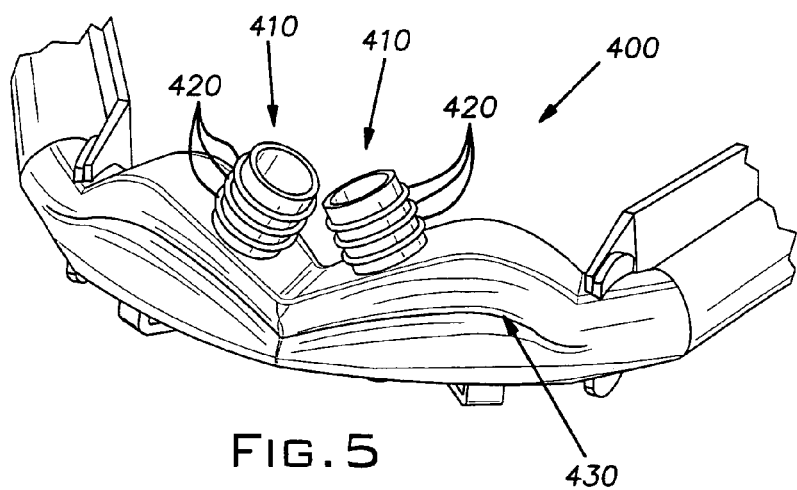
FIG. 5 illustrates a perspective view of another nasal cannula body in accordance with an aspect of the present invention.

FIG. 5 illustrates an alternative nasal cannula body 400 that can be employed with a nasal ventilation interface, such as any of those disclosed herein. Although not illustrated in detail, the nasal cannula body 400 can include headgear strap flanges for use in conjunction with headgear straps to create a first sealing interface between the nasal cannula body 400 and the patient's face. The headgear strap flanges can be configured in a manner similar to that depicted and discussed with respect to FIG. 1. The nasal cannula body 400 can also include a bellows structure 430 to create a second sealing interface between a top portion of the nasal cannula body 400 and a bottom portion of the patient's nose. The bellows structure 430 operates in a manner similar to bellows 230, described above, and thus further description of the bellows structure 430 will be omitted herein for the sake of brevity.

A third sealing interface is created by two nasal prongs 410 that project from the top portion of the nasal cannula body 400. The nasal prongs 410 comprise a substantially straight-shaped, hollow body having two or more rings 420 provided around an outer surface thereof. For example, the nasal prongs 410 can include three rings, as depicted in FIG. 4. In particular, the third sealing interface is created between an outer surface of the rings 420 and an inner surface of a patient's nares when the nasal prongs 410 are inserted into a nose of a patient. It is to be appreciated that the rings 420 can also be used in combination with the barrel-shaped nasal prongs 210 described with respect to FIG. 3.

FIG. 6 illustrates another example of a nasal cannula body 500 in accordance with an aspect of the present invention. The nasal cannula body 500 comprises a top housing portion 510 and a bottom housing portion 520. The top housing portion 510 includes a bellows structure 530 and two barrel-shaped nasal prongs 540 extending from a top surface 550 of the top housing portion 510. The barrel-shaped nasal prongs 540 and the bellows 530 are employed to create sealing interfaces between the nasal cannula body 500 and a nose of a patient. When inserted into the nares of the patient, the barrel shape of each of the prongs 540 is compressed in a radial direction such that a substantially uniform pressure is applied across its outer surface against an inner surface of a respective naris, thus forming a substantially airtight seal between the prong 540 and the naris over a large surface area. Alternatively, or additionally, two or more rings formed on the nasal prongs provide a sealing interface between the ring(s) and an inner surface of the naris. The bellows 530 act in a manner similar to a compression spring to apply a gentle upward pressure to a bottom surface of the nose, thereby holding the top surface 550 of the nasal cannula body 500 and the bottom area of the nose in sealing engagement with each other.

The bottom housing portion 520 of the nasal cannula body 500 forms a base for the bellows 530 and includes one or more air inlets 560 to which flexible air supply tubing (not shown) can be attached. The inlets 560 extend from opposing side portions of the nasal cannula body 500 in a direction angled towards the patient when the nasal cannula body 500 is in use.

Turning now to FIGS. 7 and 8, the top housing portion 510 of the nasal cannula body 500 is depicted in further detail. The top housing portion 510 has an open end 610, which serves as an air inlet, located opposite the top surface 550. Each of the barrel-shaped nasal prongs 540 is hollow and has an outlet 710 (FIG. 7) through which air pressure from the open end 610 is communicated to the patient. The top housing portion 510 further includes the bellows 530 around a circumference of the nasal cannula body 500. However, it is to be appreciated that the bellows 530 can be provided on only a front or back portion of the nasal cannula body 500, if desired.

Figure 9:
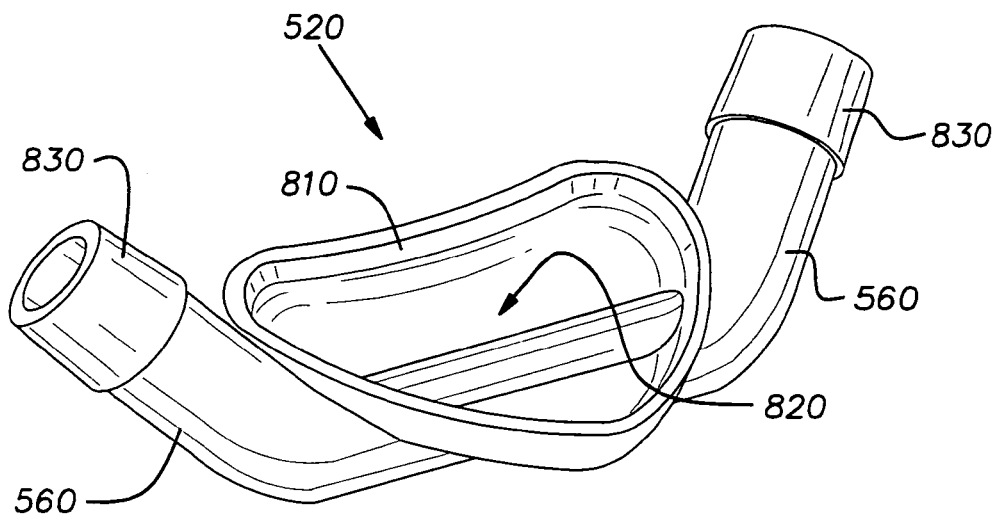
FIG. 9 illustrates a perspective view of a bottom portion of the nasal cannula body of FIG. 6 in accordance with an aspect of the present invention.
Figure 10:
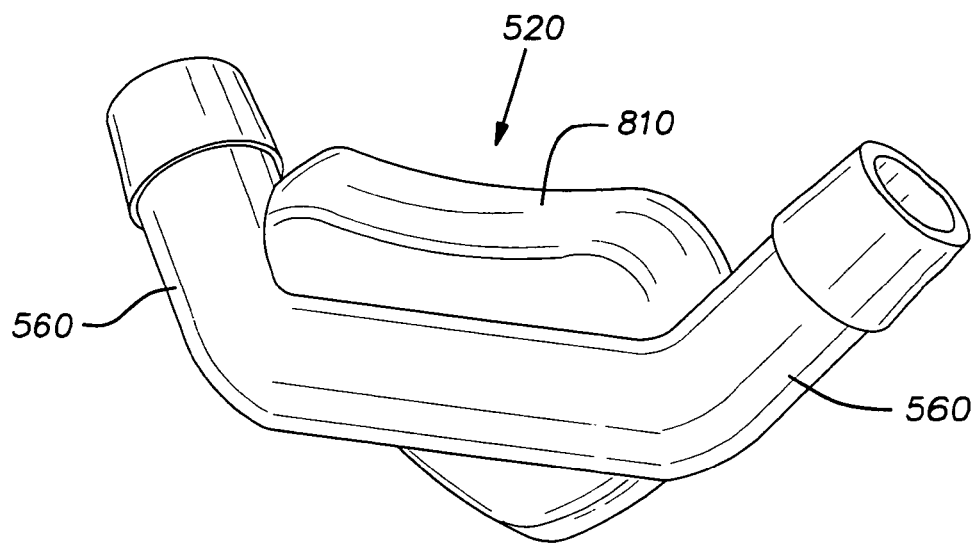
FIG. 10 illustrates another perspective view of the bottom portion of the nasal cannula body of FIG. 6 in accordance with an aspect of the present invention.

FIGS. 9 and 10 illustrate the bottom housing portion 520 of the nasal interface 500, as described with respect to FIG. 5. The bottom housing portion 520 includes a base portion 810 having an open area 820 for receiving air from the one or more air inlets 560. The air inlet(s) 560 include an end portion 830 to which flexible air supply tubing (not shown) can be attached. The air supply tubing can be made of a relatively flexible adjustable material, such as plastic or the like, and is employed as a conduit for ventilation. The nasal interface 500 can include a Y-connector having a first end adapted to receive a supply hose from a mechanical ventilator (not shown) and a second end having a pair of ports (not shown) with connectors for attachment to the air supply tubing. It is to be appreciated that the Y-connector described with respect to the present invention can alternatively be a T-connector, or any other three-way tubing connector as is known in the art. A swivel portion can also be coupled to the connector to facilitate easy manipulation of the tubing for patient comfort.

Figure 11:
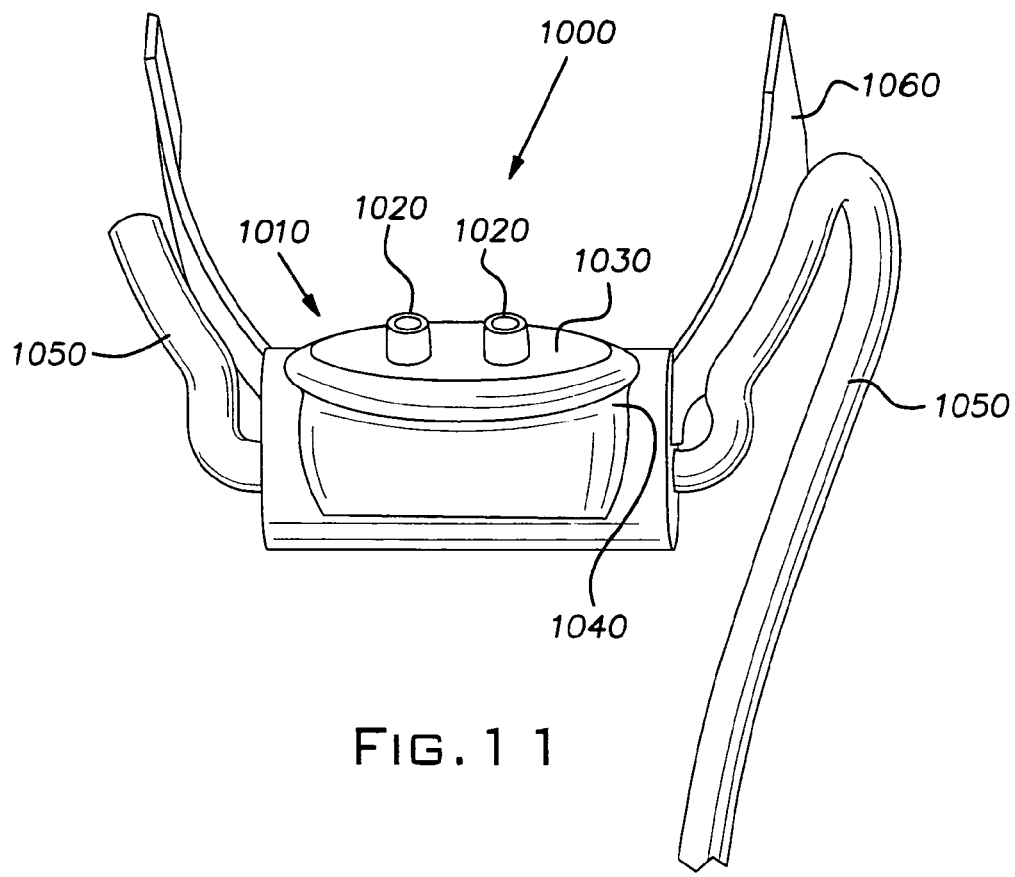
FIG. 11 illustrates a perspective view of another nasal ventilation interface in accordance with an aspect of the present invention.

Although not illustrated, it is to be appreciated that a headgear strap or a flange for a headgear strap can be coupled to the bottom housing portion 520 to provide an additional sealing interface. The headgear strap can fasten around the patient's head to apply backward pressure to the nasal cannula body 500, thereby securing it against the patient's mustache region. Also, the headgear applies an angular, upward pressure, at approximately a 45-degree angle, to the bellows 530. The spring-like feature of the bellows 530 partially absorbs this angular, upward pressure and applies gentle pressure to the bottom of the nose, thereby forming an airtight seal between the top surface 550 of the nasal cannula body 500 and the bottom of the patient's nose Turning now to FIG. 11, yet another example of a nasal ventilation interface 1000 is illustrated in accordance with another aspect of the present invention. The nasal ventilation interface 1000 includes a nasal cannula 1010 that provides at least two sealing interfaces between the nasal cannula 1010 and a patient's nose. Nasal prongs 1020, which are located on a top surface 1030 of the nasal cannula 1010, form one sealing interface. The nasal prongs 1020 can include a substantially barrel shaped structure for providing a sealing interface between an outer surface of the prongs and the inner nares of the patient. Alternatively, the nasal prongs can include a plurality of rings (not shown) formed thereon to provide a sealing interface between the rings and the inner nares of the patient. The other sealing interface is formed between the top surface 1030 of the nasal cannula 1010 and the bottom surface of the patient's nose by employing a bellows structure 1040 in conjunction with a headgear strap, as described herein. The nasal ventilation interface 1000 also includes air supply tubing 1050 to provide air to the patient via the nasal cannula. The tubing 1050 can be coupled to headgear strap flanges 1060 or can be configured to wrap around the patient's ear.

Figure 12:
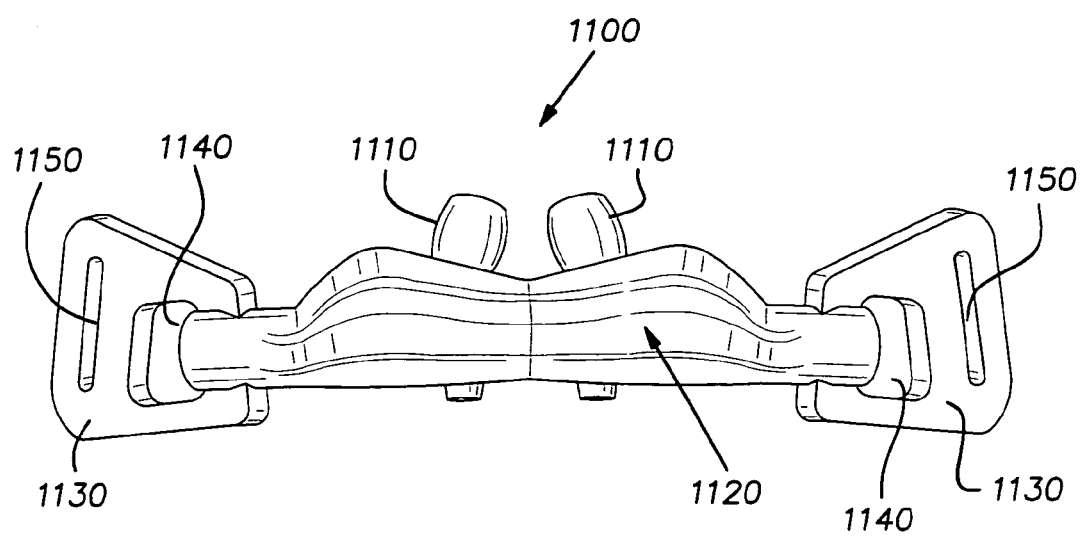
FIG. 12 illustrates a front view of another nasal cannula body in accordance with an aspect of the present invention.
Figure 13:
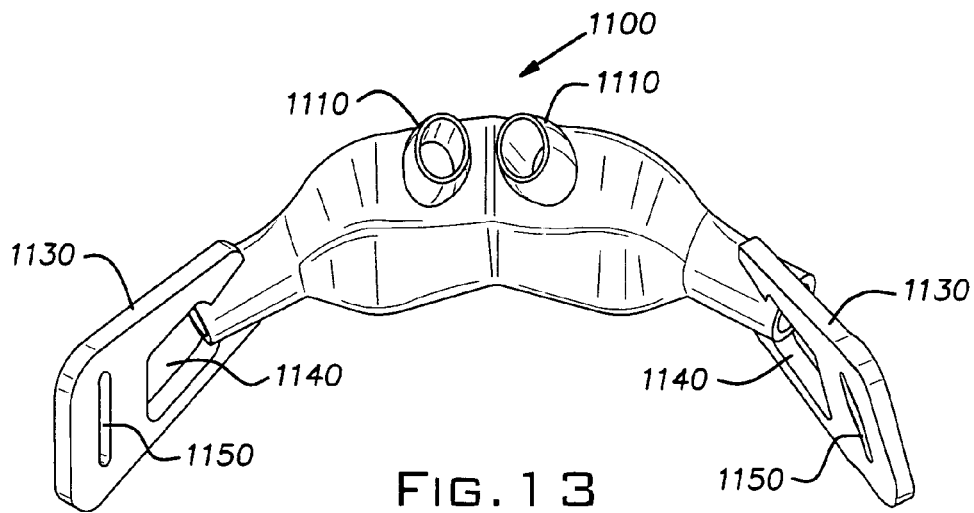
FIG. 13 illustrates a perspective view of the nasal cannula body of FIG. 12 in accordance with an aspect of the present invention.

FIGS. 12 and 13 depict yet another nasal cannula design 1100 in accordance with an aspect of the present invention. The nasal cannula 1100 includes at least one headgear strap flange 1130 materially integrally formed with the nasal cannula body 1100 to provide a first sealing interface. It is to be appreciated that the headgear strap flange 1130 can be coupled to tubes of the nasal cannula in any conventional manner. The headgear strap flange 1130 includes a first aperture 1140 for allowing air supply tubing to pass therethrough and a second aperture 1150 for receiving the headgear strap. Moreover, the flange(s) 1130 is configured such that the headgear strap secures the nasal cannula 1100 to the patient in at least two different planes: up and towards the face. The nasal cannula body 1100 further includes a bellows like structure 1120 to provide a second sealing interface between the nasal cannula body 1100 and a bottom portion of the patient's nose. Further still, the nasal cannula body 1100 includes barrel shaped nasal prongs 1110 for providing a third sealing interface between an inner surface area of the patient's nose and the nasal prongs 1110.

Figure 14:
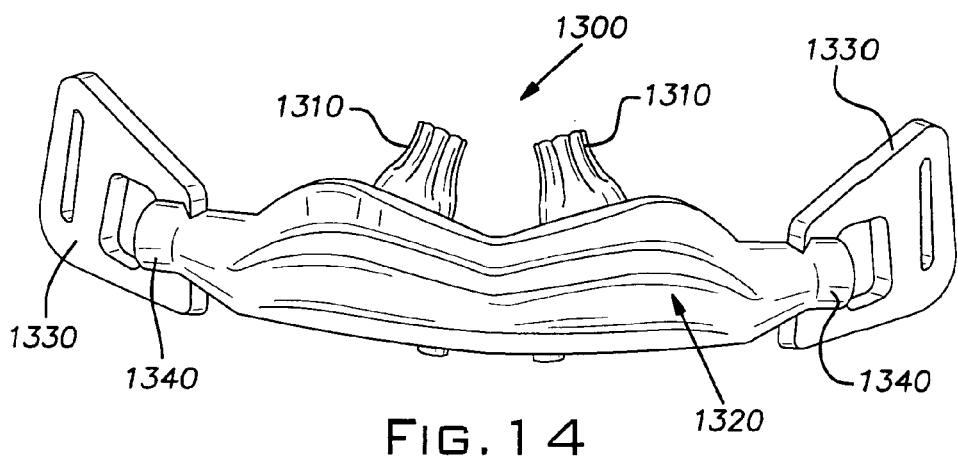
FIG. 14 illustrates a front view of another nasal cannula body in accordance with an aspect of the present invention.
Figure 15:
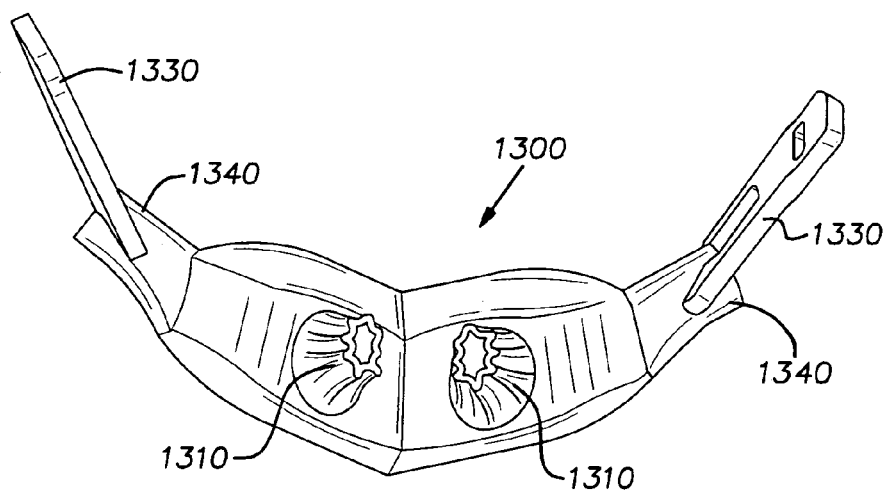
FIG. 15 illustrates a top view of the nasal cannula body of FIG. 14 in accordance with an aspect of the present invention.

FIGS. 14 and 15 illustrate another alternative nasal cannula body 1300 that can be employed with any of the nasal ventilation interfaces disclosed herein. The nasal cannula body 1300 is shaped such that it substantially conforms to contours of a patient's mustache region (see FIG. 15) and includes three sealing interfaces. One sealing interface is created by two nasal prongs 1310 projecting from a top surface of the nasal cannula body 1300. The nasal prongs 1310 have thin, ribbed walls, which are adapted to inflate under pressure. For example, the nasal prongs 1310 can be easily and comfortably inserted into a nose of a patient in a compressed state, as illustrated in FIGS. 14 and 15. Then, when a gas flows through the ventilation interface via a CPAP machine, for example, the nasal prongs 1310 can inflate to create an air tight sealing surface between the outer surface of the nasal prongs 1310 and the nares of the patient. The nasal prongs 1310 can assume a barrel-shaped structure when inflated to provide a large, even sealing surface in the nares. However, it is to be appreciated that the nasal prongs 1310 can assume any suitable shape when inflated to provide maximum sealing between the prongs 1310 and the nares.

Another sealing interface is created by a bellows-like structure 1320 formed on a front portion of the nasal cannula body 1300. The bellows-like structure 1320 operates to apply a gentle upward pressure to the nose such that a top surface of the nasal cannula body 1300 is held in sealing engagement with a bottom surface of a nose. The bellows 1320 is adjustable in length between a contracted state and an expanded state. It is to be appreciated that the bellows can additionally, or alternatively, be located on a back portion of the nasal cannula body 1300.

Integral headgear strap flanges 1330 create yet another sealing interface. The headgear strap flanges 1330 are located at an angle suitable to provide a backward pressure to secure the body 1300 against the patient's mustache region in addition to an upward pressure to secure the body 1300 against the patient's nose. For example, the headgear strap flanges 1330 can be located at approximately a 45-degree angle with respect to a central axis of inlet ports 1340 located on the nasal cannula body 1300. The spring-like feature of the bellows 1320 partially absorbs this upward pressure and applies gentle pressure to the bottom the nose, thereby, forming an airtight seal between the top surface of the nasal cannula body 1300 and the bottom of the patient's nose.

Figure 16:
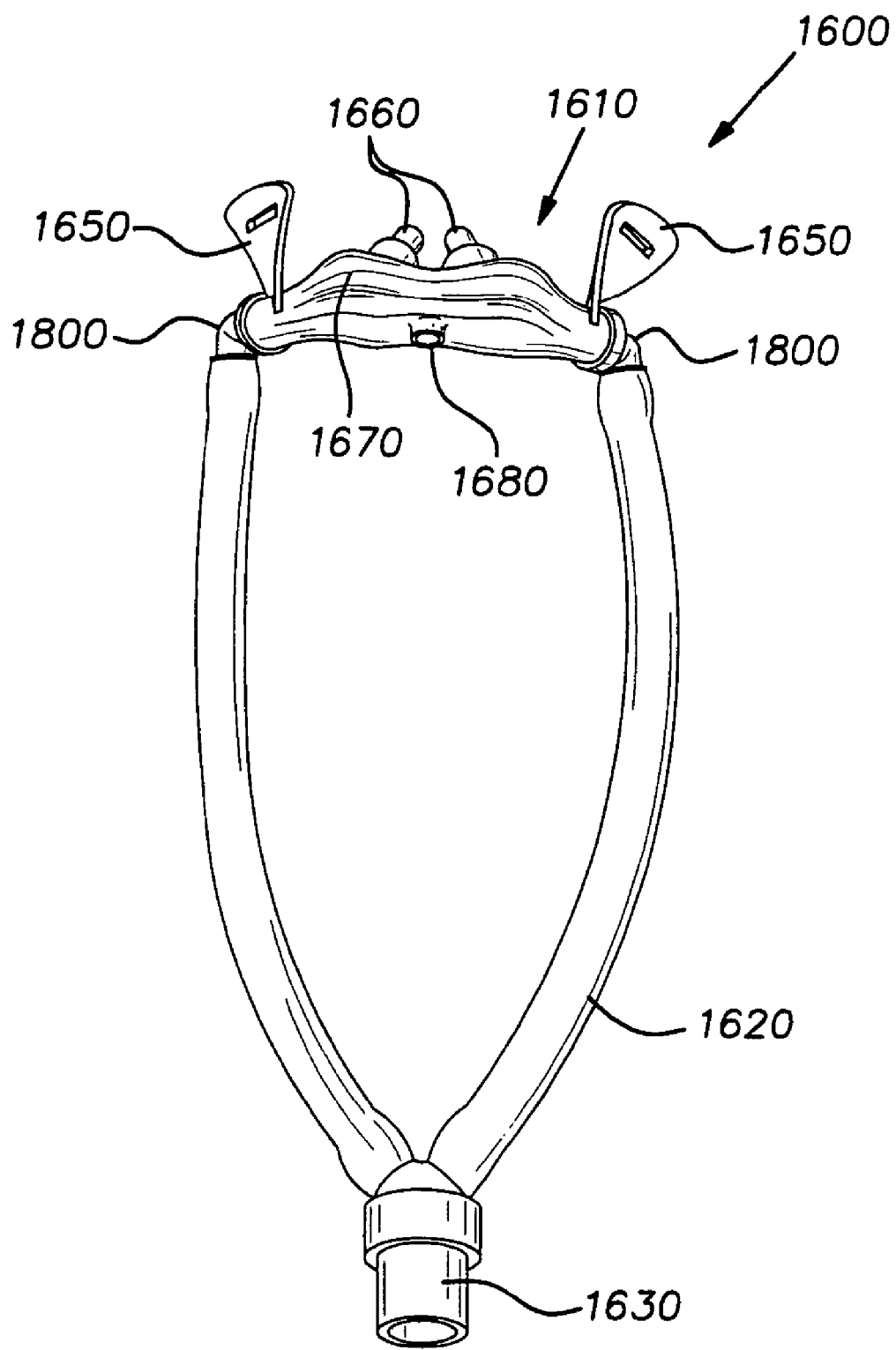
FIG. 16 illustrates a perspective view of another nasal ventilation interface in accordance with an aspect of the present invention.

Turning now to FIG. 16, another example of a nasal ventilation interface 1600 is depicted in accordance with an aspect of the present invention. The nasal ventilation interface 1600 includes three different sealing interfaces and three different swivel points for patient comfort. The nasal ventilation interface 1600 includes a nasal cannula body 1610 that is connected to a ventilation device (not shown) via at least one supply tube 1620. A first swivel component 1630 is utilized to couple the at least one supply tube 1620 with a ventilation device supply tube (not shown). The first swivel component 1630 is similar in construction to the swivel component described with respect to FIG. 2 herein and thus will not be described further for the sake of brevity.

Figure 17:
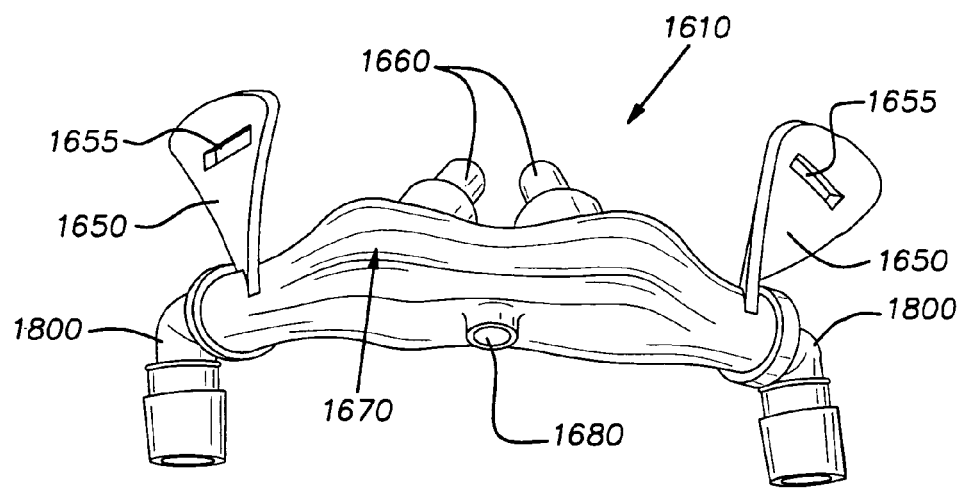
FIG. 17 illustrates a perspective view of a nasal cannula body employed in the nasal ventilation interface of FIG. 16 in accordance with an aspect of the present invention.

FIG. 17 illustrates the nasal cannula body 1610 in greater detail. A first sealing interface of the nasal ventilation interface 1600 is created by at least one headgear strap flange 1650, which can be formed materially integrally with the nasal cannula body 1610. The headgear strap flange(s) 1650 includes at least one slot 1655 formed therein for securing the headgear strap thereto. Due to the configuration of the headgear strap flange 1650, the headgear strap, when worn by the patient, applies a backward pressure to the nasal cannula body 1610. The first sealing interface is thus created between the nasal cannula body 1610 and the patient's mustache region. In addition to this backward pressure, the flange(s) 1650 is positioned in such a way that the headgear strap applies an angular, upward pressure (e.g., approximately a 45-degree angle) to a bellows portion 1670 of the nasal cannula body 1610, which will be described in further detail below. This angular, upward pressure creates a second sealing interface between a top surface of the nasal cannula body 1610 and a bottom surface of the patient's nose.

A third sealing interface is created by a pair of nasal prongs 1660 projecting from a top surface of the nasal cannula body 1610. The nasal prongs 1660 include a bulbous base portion that tapers into a substantially straight top portion. The nasal prongs 1660 are inserted into the nares of the patient such that the bulbous base portion of the nasal prongs 1660 creates a substantially airtight seal between an outer surface area of the base portion and an inner surface area of the nares. At least one bleeder port 1680 projects from a bottom surface of the nasal cannula body 1610.

The nasal cannula body 1610 further comprises at least one inlet for receiving gas from the supply tube(s) 1620. In the illustrated example, the nasal cannula body 1610 includes two inlets coupled to two supply tubes 1620. Two swivel elbows 1800 are also included to provide an airtight coupling between the nasal cannula body 1610 and the supply tubes 1620, as well as, to provide an additional swivel feature to the nasal ventilation interface 1600. The swivel elbows 1800 swivel about an axis parallel to a central axis of the inlet ports; thereby, allowing the supply tubes 1620 to swivel 360° about the nasal cannula body 1610. Thus, the patient can wear the nasal ventilation interface 1600 with the supply tubes 1620 down towards their chest or above their head. Further, the swivel elbows 1800 allow the nasal cannula body 1610 to self-adjust to a correct angle for nasal prong insertion in both the downward and over the head positions.

Figure 18:
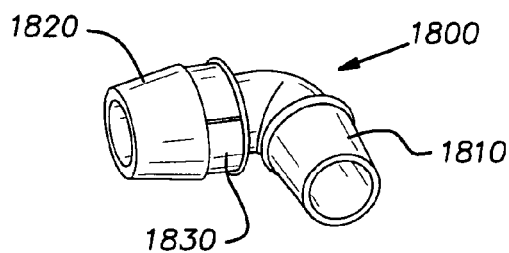
FIG. 18 illustrates a perspective view of an elbow component in accordance with an aspect of the present invention.
Figure 19:
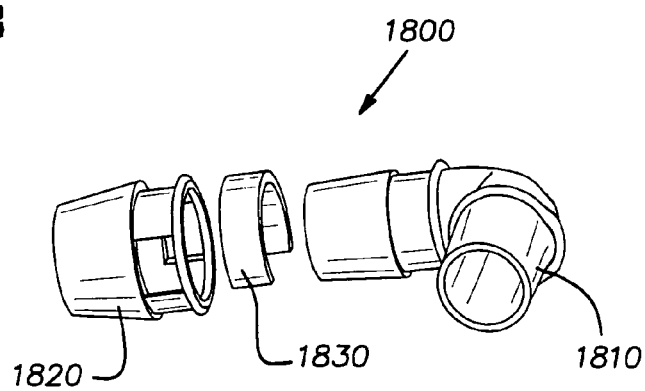
FIG. 19 illustrates an exploded view of the elbow component of FIG. 18 in accordance with an aspect of the present invention.

The swivel elbows 1800 are illustrated in further detail in FIGS. 18 and 19. The swivel elbows 1800 can be manufactured from a rigid plastic material, or any other suitable material, and include an elbow component 1810, a swivel connector 1820, and a locking collar 1830. The swivel connector 1820 fits over an end portion of the elbow component 1810. The locking collar 1830 snaps over a portion of the swivel connector 1820 such that at least one small protrusion (not shown) on the locking collar 1830 projects through a corresponding aperture on the swivel connector 1820 to make contact with the elbow component 1810, thereby locking the three components 1810, 1820, and 1830 together. The swivel connector 1820 and the locking collar 1830 are then operable to rotate about the end portion of the elbow component 1810. It is to be appreciated that any suitable size and shape swivel component can be employed to couple at least one supply tube to the nasal cannula body and is contemplated as falling within the scope of the present invention.

Figure 20:
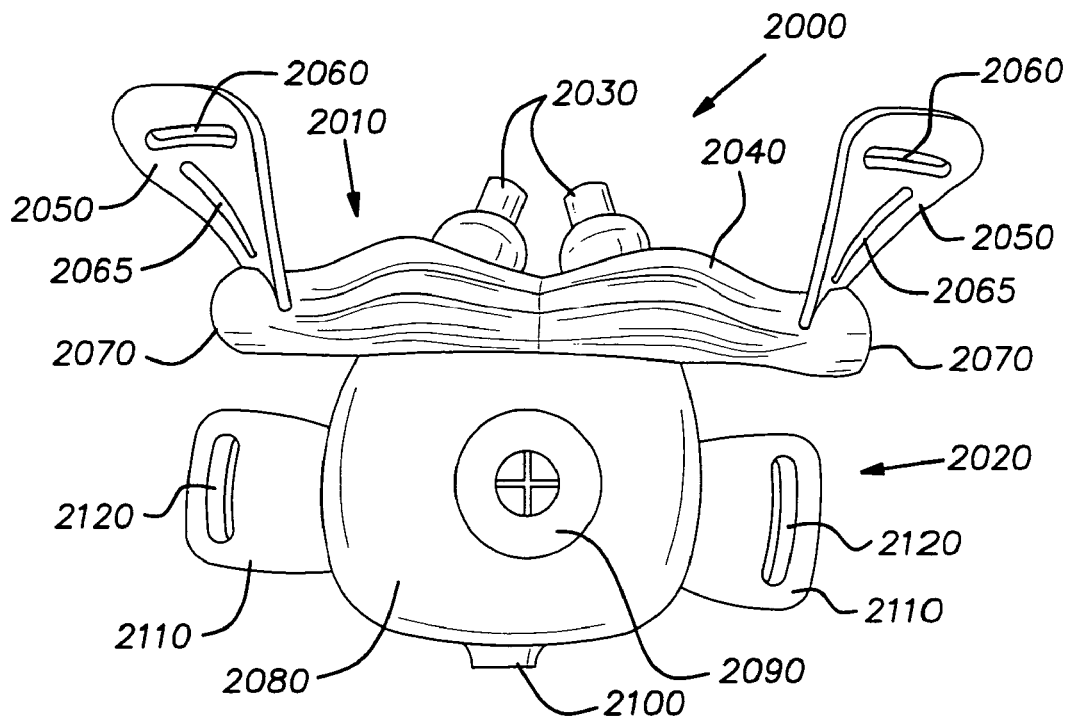
FIG. 20 illustrates a perspective view of a combination face mask and nasal cannula body in accordance with an aspect of the present invention.
Figure 21:
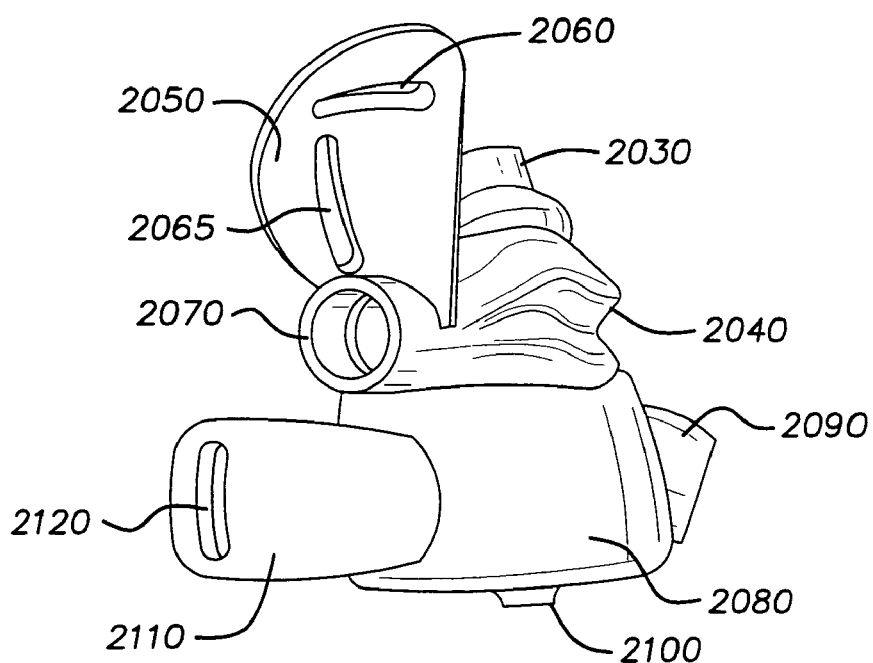
FIG. 21 illustrates another perspective view of the combination face mask and nasal cannula body of FIG. 20 in accordance with an aspect of the present invention.

FIGS. 20 and 21 illustrate yet another example of a nasal ventilation device 2000. The nasal ventilation device 2000 is a hybrid of a nasal cannula body portion 2010 and a face mask portion 2020. The nasal cannula body portion 2010 includes a pair of nasal prongs 2030 for insertion into a patient's nares. The nasal prongs 2030 can include a bulbous-shaped base portion to facilitate providing an airtight seal between an outer surface of the nasal prongs 2030 and an inner surface of the patient's nares. The bulbous-shaped base portion includes a large sealing surface area to mitigate internal pressure points between the nasal prongs 2030 and the nares, thereby mitigating nasal irritation in the patient. Moreover, when gas flows through the nasal prongs 2030, the nasal prongs 2030 are adapted to expand to further seal the nasal prongs 2030 within the nares. The bulbous-shaped base portion of the nasal prongs 2030 tapers into a straight-shaped end portion. It is to be appreciated that the nasal prongs 2030 can be of any suitable shape for providing a sealing interface between the prongs and the patient's nares. For example, the nasal prongs 2030 can be barrel-shaped. At least one inlet 2070 is included on the nasal cannula body portion 2010 for receiving the gas from the ventilation device (not shown).

The nasal cannula body portion 2010 further includes a bellows 2040 formed within the nasal cannula body portion 2010 to facilitate sealing between a top surface of the nasal cannula body portion 2010 and a bottom surface of a patient's nose. Headgear strap flanges 2050 are also integrally formed with the nasal cannula body portion 2010 to facilitate yet another sealing interface between the nasal cannula body portion 2010 and the patient. The headgear strap flanges 2050 each include at least one aperture, and in this example, each of the headgear strap flanges 2050 includes two apertures 2060 and 2065. The apertures 2060 and 2065 receive headgear straps, which are then fastened around the patient's head. The position of the headgear strap flanges 2050, as well as the positions of the apertures 2060 and 2065, pull the nasal cannula body portion 2010 backwards and upwards towards the patient's face to create a sealing interface between a back portion of the nasal cannula body 2010 and the patient's mustache region.

The face mask portion 2020 of the ventilation device 2000 includes an elastomeric material and is shaped so as to fit the contours of a patient's face around a mouth area of the patient. The face mask portion 2020 also includes headgear strap flanges 2110 formed integrally with the mask 2020 to facilitate sealing of the mask against the patient's face. The headgear strap flanges 2110 each include at least one aperture 2120 for receiving headgear straps. The face mask portion 2020 further includes at least one bleeder port 2100 and an anti-asphyxcsia valve 2090.

Due to the three different sealing means of a nasal ventilation interface, as described with respect to the plurality of embodiments described herein, an adequate seal is provided with minimal pressure concentration being applied to the patient's nose and face; thereby, mitigating mucosal irritation. Accordingly, effectiveness as well as comfort of the nasal ventilation interface is achieved.

Although a detailed description of a preferred embodiment of this invention has been shown and described hereinabove, it will be understood that various modifications and rearrangements of the parts and their respective features may be resorted to without departing from the scope of the invention as disclosed herein.

What is claimed is:

1. A ventilation interface comprising:
a nasal cannula body, the nasal cannula body comprising:
   a pair of nasal prongs located on a top portion of the nasal cannula body to create a first sealing interface between the nasal cannula body and a nose; and
   a bellows-like structure integrally molded in a portion of the nasal cannula body, wherein the bellows-like structure is configured to contact a bottom surface of the nose to create a second sealing interface between the nasal cannula body and the nose.

2. The ventilation interface of claim 1, wherein the nasal prongs include two or more rings provided thereon to create a sealing surface between an outer surface of the rings and an inner surface of a patient's nares.

3. The ventilation interface of claim 1, wherein the nasal prongs include a thin, ribbed wall that inflates under pressure.

4. The ventilation interface of claim 3, wherein the nasal prongs are substantially barrel-shaped when inflated under pressure.

5. The ventilation interface of claim 1, wherein the nasal prongs include a bulbous-shaped base portion.

6. The ventilation interface of claim 5, wherein the bulbous-shaped base portion tapers into a straight-shaped end portion.

7. The ventilation interface of claim 1, wherein the first sealing interface is created between an outer surface area of the nasal prongs and a patient's nares.

8. The ventilation interface of claim 1, wherein the second sealing surface is created between a top surface of the nasal cannula body and a bottom, triangular shaped area of the nose.

9. The ventilation interface of claim 1, wherein the bellows-like structure is integrally formed in a front portion of the nasal cannula body and a back portion of the nasal cannula body is substantially straight-shaped.

10. The ventilation interface of claim 1, wherein the nasal cannula body further comprises a pair of bleeder ports located at a bottom portion of the nasal cannula body.

11. The ventilation interface of claim 1, wherein the nasal cannula body further comprises a top housing portion and a bottom housing portion, the top housing portion having the bellows-like structure integrally molded therein.

12. The ventilation interface of claim 1, further comprising a pair of supply tubes for delivering a gas to a patient via the nasal cannula body.

13. The ventilation interface of claim 12, wherein the supply tubes are formed integrally with the nasal cannula body.

14. The ventilation interface of claim 12, wherein the supply tubes are coupled to the nasal cannula body via at least one swivel component.

15. The ventilation interface of claim 1, further comprising a pair of flanges for securing a headgear strap thereto.

16. The ventilation interface of claim 15, wherein the flanges are formed integrally with the nasal cannula body.

17. The ventilation interface of claim 15, wherein a first flange is formed integrally with a first inlet port of the nasal cannula body and a second flange is formed integrally with a second inlet port of the nasal cannula body.

18. The ventilation interface of claim 15, wherein the flanges are positioned at an angle of about 45-degrees with respect to a central axis of an inlet port formed integrally with the nasal cannula body.

19. The ventilation interface of claim 1, wherein a main portion of the nasal cannula body is shaped to conform to a mustache area of a patient's face.

20. A ventilation interface comprising:
a nasal cannula body; and
a pair of barrel shaped prongs located on a top portion of the nasal cannula body, the barrel shaped prongs having a largest diameter at a midsection of each of the prongs and smaller diameters at first and second ends of each of the prongs and providing a large sealing surface between an outer surface of the prongs and an inner surface of a patient's nares,
wherein the largest diameter of the barrel shaped prongs is configured to fit substantially entirely within the patient's nares such that the largest diameter of the prongs compresses in a radial direction and applies substantially uniform pressure across the outer surface of the prongs and the inner surface of the patient's nares.

21. The ventilation interface of claim 20 wherein the barrel shaped prongs comprise a thin, ribbed wall that inflates under pressure to create the sealing surface.

22. The ventilation interface of claim 20, further comprising a pair of flanges formed integrally with the nasal cannula body.

* * * * *